United States Patent [19]

Holloway et al.

[11] 3,953,486
[45] Apr. 27, 1976

[54] MANUFACTURE OF LEAD STYPHNATE

[75] Inventors: Kenneth John Holloway, Sandringham; John Michael Jenkins, Chingford; George William Charles Taylor, Waltham Abbey, all of England

[73] Assignee: The Secretary of State for Defence in Her Britannic Majesty's Government of the United Kingdom of Great Britain and Northern Ireland, London, England

[22] Filed: Feb. 6, 1973

[21] Appl. No.: 330,083

[30] Foreign Application Priority Data
June 9, 1972  United Kingdom............... 27052/72

[52] U.S. Cl............................................. 260/435 A
[51] Int. Cl. .................................................. C07f 7/24
[58] Field of Search................................. 260/435 A

[56] References Cited
UNITED STATES PATENTS

| | | | |
|---|---|---|---|
| 1,443,328 | 1/1923 | Herz | 260/435 A X |
| 1,999,728 | 4/1935 | Herz | 260/435 A |
| 2,150,653 | 3/1939 | Franz | 260/435 A |
| 2,295,104 | 9/1942 | Garfield | 260/435 A |
| 2,493,549 | 1/1950 | Rubenstein | 260/435 A |
| 3,002,012 | 9/1961 | Backensto | 260/435 A |
| 3,041,361 | 6/1962 | Komarmy | 260/435 A |

OTHER PUBLICATIONS

Chemical Abstracts, Vol. 18, 167,168 (1924).
Chemical Abstracts, Vol. 72, 21427w (1970).
McCrone et al., Analytical Chemistry, Vol. 27, pp. 2014–2015 (1955).

*Primary Examiner*—H. Sneed
*Attorney, Agent, or Firm*—Stevens, Davis, Miller & Mosher

[57] ABSTRACT

A process for the preparation of $\alpha$ normal lead styphnate by reacting at an elevated temperature an aqueous solution containing lead cations with a solution containing styphnate ions in the presence of a mineral acid present in the range about 1 to about 15 grammes of mineral acid to 1 liter of the solution containing the styphnate ions.

14 Claims, No Drawings

MANUFACTURE OF LEAD STYPHNATE

This application relates to the preparation of lead styphnate ($\alpha$ normal lead trinitroresorcinate).

Normal lead styphnate finds an extensive use in the explosives industry, particularly as an ingredient of primers and detonators and its economic and efficient manufacture is of great importance. It has been precipitated by the addition of a soluble lead salt to a solution containing styphnate ions. The chemistry of the process is complex and the main problems involved are associated with the formation of basic salts, polymorphs and viscous gels and other conditions leading to crystals of unsatisfactory physical form. A feature of a product containing very small or broken crystals is that its explosive hazard is greatly increased. Many of these problems have been overcome in previous processes by using dilute solutions and/or two-stage precipitations and both are wasteful in terms of product output. In some processes, the pH of the reaction solution, control of which is vital to prevent the persistence of basic salts, has been achieved by either the addition of weak organic acids, for example acetic acid, or by an excess of stpyhnic acid.

In the previous processes, there has been a compromise between the technical quality of the product on the one hand and yields and economy of the process on the other hand, for example, dilute solutions, two-stage processes and/or purified styphnic acid have all been employed to improve the physical form of the product at the expense of economy.

In the present process, high quality of product has been combined with high yield on cheap reactants and on plant capacity and process time.

It has now been found that $\alpha$ normal lead styphnate of good quality with respect to chemical purity, crystal shape and size, may be prepared cheaply in a one-stage process by reacting at an elevated temperature a soluble lead salt with a solution containing styphnate ions in the presence of added mineral acid. The mineral acid may be added to one or both of the reacting solutions or independently to the reaction vessel. Solutions of the order of 1 molar are normally used and the mineral acid should be present in the range from about 1 to 15 grms to a liter of a molar solution of styphnate ions or the equivalent when added wholly or partly to the soluble lead salt or independently.

According to the invention, there is provided a process for the preparation of $\alpha$ normal lead styphnate comprising reacting at an elevated temperature an aqueous solution containing lead cations with a solution containing styphnate ions in the presence of a mineral acid present in the range about 1 to about 15 grammes of mineral acid to 1 liter of the solution containing the styphnate ions.

Preferably the mineral acid is present in the range about 1 to about 5 grammes of acid to 1 liter of the solution containing the styphnate ions.

Preferably the solution containing a soluble lead salt is added to the solution containing styphnate ions.

Preferably the mineral acid is present in the styphnate solution before the addition of the solution containing the soluble lead salt.

Preferably the reaction temperature is at least 50°C.

The mineral acid selected for the addition should preferably be such that it does not react with the soluble lead salt under the reaction conditions to form an insoluble precipitate and preferably the mineral acid is nitric acid. Other mineral acids which may be used are hydrochloric acid and sulphuric acid. An insufficient quantity of added mineral acid will give an inferior process and product due to formation of basic and ill-defined salts and poor nucleation give a wide range of particle size and shape. An excess quantity of mineral added will give reduced yields of product.

It will be realised that soluble salts of styphnic acid may be prepared from non-stoichiometric quantities of reactants and thus their aqueous solutions may be alkaline. The solution containing the styphnate ions should therefore be conditioned prior to its addition to the process of the invention, to lie within the pH range 6.8 to 8.0 preferably 7.2 to 7.5.

In carrying out the process according to the invention, it is preferred to use magnesium styphnate as the soluble styphnate salt. The solution containing magnesium styphnate may be conveniently prepared by the interaction of a suspension of styphnic acid in water and heavy magnesium carbonate or magnesium oxide or magnesium hydroxide at an elevated temperature.

One advantage of the new process according to the invention is that the styphnate salt, for instance magnesium styphnate, may be prepared from cheap, crude, unrecrystallised styphnic acid.

A survey of the published literature was carried out to give a comparison of the yield, where this is applicable, of lead styphnate when prepared by various known processes and the process of the present invention. The published literature is in many ways incomplete and no precise details can be given.

The processes are as follows:

A. Example I of the present invention.

B. Lead nitrate added to a magnesium styphnate solution containing an excess of styphnic acid (Chemistry and Technology of Explosive Vol 3 p. 218 T Urbanski, Pergammon Press, Polish Scientific Publishers, Warsaw, 1967).

C. Sodium styphnate made from either crude styphnic acid or styphnic acid containing at least one mononitro derivative of resofurin, indophenol or resazurin treated with a solution of lead nitrate containing acetic acid (British Pat. No. 519340).

D. A lead acetate solution added to a suspension of styphnic acid in water at temperatures in range 40–70 (U.S. Pat. No. 2,295,104).

E. Lead nitrate solution added to magnesium styphnate solution containing excess styphnic acid (National Technical Information Service, U.S. Dept. Commerce, Report PB 95613)

The results are given in the table.

| Process | Yield per batch (moles) | % yield on styphnic acid | % yield on $Pb^{++}$ | Yield per liter of production capacity (moles) | Yield per minute of precipitation time (moles) |
| --- | --- | --- | --- | --- | --- |
| A | 19.2 | 93 | 93 | 0.472 | 0.96 |
| B | 17.2 | + | 74 | 0.156 | 0.58 |
| C* | 1.8 | | | 0.235 | 0.038 |

-continued

| Process | Yield per batch (moles) | % yield on styphnic acid | % yield on Pb++ | Yield per liter of production capacity (moles) | Yield per minute of precipitation time (moles) |
| --- | --- | --- | --- | --- | --- |
| D | 3.1 | 93 | 93 | 0.326 | 0.258 |
| E | 7.7 | 79 | 57 | 0.146 | 0.385 |

*It is assumed that there is a 100% yield on styphnic acid.
†insufficient data given to estimate In spite of the paucity of results in the prior art, it will be seen that the new process has much higher yields in every respect. That is the yield of total product and the yield on plant capacity is much greater. The high yield of product based on the original reactants considerably reduces the possibility of polution from the effluents of the plant.

The invention is illustrated, by way of further explanation, by the following Examples.

EXAMPLE 1

A magnesium styphnate solution was prepared by the steps of adding 27.5 kg (dry weight) of styphnic acid to 70 liters of distilled water, warming the solution to 45°C, and then adding 11.3 Kg magnesium carbonate (heavy) in small quantities with stirring. The temperature was increased to 55°–60°C and stirring was continued until solution was complete. The solution was cooled, the volume adjusted to 110 liters, filtered and the pH was found to be above 7.2. An analysis of this solution showed that it contained 245g styphnate ion (as styphnic acid) per liter. 330 ml of nitric acid (sp gr 1.42) was then added with stirring.

A lead nitrate solution was made by adding 37.4 Kg of crystalline lead nitrate to 100 liters of distilled water, warming the solution to about 50°C and stirring until disolved. The solution was cooled, the volume adjusted to 110 liters and filtered. The solution was analysed and distilled water added until the concentration of lead nitrate was 331.2g g/l (sp gr 20° about 1.279) (pH 3.3 – 3.4).

20 litres of the above prepared magnesium styphnate solution was measured into a stainless steel tank and its temperature raised to 80° with stirring, 20 liters of the prepared lead nitrate solution was added over a period of 20 minutes whilst the temperature was maintained at 80°C. After being held for 5 minutes the solution was cooled to 45°C and the mother liquor decanted. The product was washed by decantation and filtered. Yield 93%. The product had a bulk density of 1.54 g/ml and was of uniform particle size with good flowing properties. The lead styphnate content by chemical analysis was greater than 99.5 per cent.

EXAMPLE 2

To a liter of a molar solution of magnesium styphnate prepared as in Example 1 was added 1.3 ml of nitric acid (sp gr 1.42) with stirring. 200 ml of the resultant solution was heated to 80°C with stirring and to it was added 200 ml of a lead nitrate solution (331.2 g/l) over a period of 20 minutes. After completion of the addition, the solution was stirred for a further 5 minutes, cooled to 45°C and the mother liquor decanted. The product was washed by decantation and filtered to give a yield of 87.2g (93.2%). The product had a bulk density of 1.48 g/ml and was of uniform particle size with good flowing properties.

EXAMPLE 3

To a liter of a molar solution of magnesium styphnate prepared as in Example 1 was added 3.8 ml of concentrated hydrochloric acid (sp gr 1.18) with stirring. 200 ml of the resultant solution was heated to 80°C with stirring and to it was added 200 ml of a lead nitrate solution (331.2 g/l) over a period of 20 minutes. After completion of the addition, the solution was stirred for a further 5 minutes, cooled to 45°C and the mother liquor decanted. The product was washed by decantation and filtered to give a yield of 86.7 g (92.7%). The product had a bulk density of 1.54 g/ml and was of uniform particle size with good flowing properties.

EXAMPLE 4

Further preparations were carried out using the method as given in Example 3 except that the amount of nitric acid was varied. The yields of lead styphnate from these preparations are given in the following Table.

| Free nitric acid content of magnesium styphnate solution g/l | Weight percent yield of lead styphnate |
| --- | --- |
| 1.0 | 93.2 |
| 1.1 | 92.7 |
| 2.5 | 93.2 |
| 9.5 | 83.3 |
| 14.8 | 74.8 |

In all the preparations, the lead styphnate produced was of uniform size with good flowing properties.

What we claim is:

1. A process for the preparation of $\alpha$ normal lead styphnate comprising reacting at an elevated temperature an aqueous solution containing lead nitrate with a solution containing magnesium styphnate in the presence of a mineral acid present in the range about 1 to about 15 grams of mineral acid to 1 liter of the solution containing the magnesium styphnate.

2. A process according to claim 1 wherein the solution containing the lead nitrate is added to the solution containing the magnesium styphnate.

3. A process according to claim 2 wherein the mineral acid is present in the styphnate solution before the addition of the solution containing the lead nitrate.

4. A process according to claim 1 wherein the reaction temperature is at least 50°C.

5. A process according to claim 1 wherein the mineral acid is selected from the group consisting of nitric acid, hydrochloric acid and sulphuric acid.

6. A process according to claim 1 wherein the solution containing magnesium styphnate is conditioned, prior to its addition to the process of the invention, to lie within the pH range 6.8 to 8.0.

7. A process according to claim 6 wherein the pH range is 7.2 to 7.5.

8. A process for the preparation of α normal lead styphnate comprising reacting at an elevated temperature an aqueous solution containing lead nitrate and an aqueous solution containing magnesium styphnate in the presence of a mineral acid present in the range of about 1 to about 5 grams of mineral acid to 1 liter of the solution containing the magnesium styphnate.

9. A process according to claim 8 wherein the solution containing the lead nitrate is added to the solution containing the magnesium styphnate.

10. A process according to claim 9 wherein the mineral acid is present in the magnesium styphnate solution before the addition of the solution containing the lead nitrate.

11. A process according to claim 8 wherein the reaction temperature is at least 50°C.

12. A process according to claim 8 wherein the mineral acid is selected from the group consisting of nitric acid, hydrochloric acid and sulphuric acid.

13. A process according to claim 8 wherein the solution containing magnesium styphnate is conditioned, prior to its addition to the process of the invention, to lie within the pH range 6.8 to 8.0.

14. A process according to claim 13 wherein the pH range is 7.2 to 7.5.

* * * * *